United States Patent [19]

Guguen-Guillouzo et al.

[11] Patent Number: 5,112,757
[45] Date of Patent: May 12, 1992

[54] METHOD FOR OBTAINING HUMAN HEPATOCYTE CULTURES

[75] Inventors: Christiane Guguen-Guillouzo; André Guillouzo; Michel Bourel, all of Rennes, France

[73] Assignee: Institut National de la Sante et de la Recherche, Paris, France

[21] Appl. No.: 34,983

[22] Filed: Apr. 6, 1987

Related U.S. Application Data

[63] Continuation of Ser. No. 694,518, Dec. 27, 1984, abandoned.

[30] Foreign Application Priority Data

Apr. 29, 1983 [FR] France ............................. 83 07148

[51] Int. Cl.⁵ .................................................. C12N 5/08
[52] U.S. Cl. .............................. 435/240.2; 435/240.21
[58] Field of Search .................... 435/42, 267, 240.2, 435/240.21, 240.25, 284, 948

[56] References Cited

U.S. PATENT DOCUMENTS 3,935,066 1/1976 Apostolov ................. 435/240.23

OTHER PUBLICATIONS

News article (France) "La voie des cellules de culture" Newspaper: La Vie Scientifique, Jan. 30, 1987.
Baffet et al., *Biochem. Biophys. Res. Comm.* 109: 507–512, (1982).
Guillouzo et al., *Triangle* 20: 121–128, (1981).
Guguen-Guillouzo et al., *Exp. Cell Res.* 143:47–54, (1983).

*Primary Examiner*—Douglas W. Robinson
*Assistant Examiner*—Marian C. Knode
*Attorney, Agent, or Firm*—Cushman, Darby & Cushman

[57] ABSTRACT

A method for culturing human hepatocytes is disclosed. The method comprises associating a culture of human hepatocytes including a medium with cells of hepatic origin, these cells being different from the hepatocytes and being of the type insuring in vivo specific cellular interactions with the hepatocytes. The culture obtained maintains hepatocyte functions at a high level for an extended period of time.

27 Claims, 5 Drawing Sheets

HEPATOCYTES 0,5μ

HEPATIC
EPITHELIAL
CELLS

METHOD FOR OBTAINING HUMAN HEPATOCYTE CULTURES

This is a continuation of application Ser. No. 694,518 filed Dec. 27, 1984, now abandoned.

The invention relates to a method for obtaining human hepatocyte cultures, the cultures obtained thereby and their biological and biochemical applications.

It is known that the liver constitutes the site of multiple functions. The interest of human hepatocyte cultures is therefore understood since these cultures are useful in particular both for pharmacological studies concerning, for example, the toxicity and metabolism of a new molecule and in virology for the study, for example, of viral hepatitis.

In this regard it is important to be able to have available homogenous populations.

In the same way, the interest in having available normal cell cultures having a normal karyotype will be appreciated.

Now the studies, few in number, carried out hitherto on human liver cultures have been performed mostly on tissue fragments, derived principally from pathological livers or hepatoma lines, and resulting in heterogeneous populations.

According to recent techniques, viable hepatocytes have been obtained by enzymatic perfusion of hepatic fragments derived mostly from sub-normal pathological livers.

However, hepatocytes placed in suspension cannot survive more than some hours and hence do not permit long-term studies. In culture, it has been observed that hepatocytes of small mammals only maintain a stable phenotype for some days at the most.

The addition to the culture medium of suitable nutrient substances and the use of organic substrates enable survival to be prolonged but without the maintenance, quantitatively, of the specific functions of the liver.

In recent studies, the inventors have obtained a prolonged survival of rat hepatocyte cultures, with maintenance of their functional integrity for several weeks, associating the rat hepatocytes with a hepatic cell, probably of biliary origin, from the same species.

The state of advance of the research of the inventors in this field, who have also perfected a method for isolating normal human hepatocytes in large amounts, has led them to study new means for obtaining human hepatocyte cultures corresponding more satisfactorily to the exigencies of the technique.

Surprisingly, the use of a specific environment with respect to human hepatocytes has proved to confer on these hepatocyte cultures properties distinctly superior to those obtained hitherto.

It was therefore an object of the invention to provide a longterm culture method for human heptocytes.

It was also an object to provide human hepatocyte cultures capable of maintaining specific hepatocyte functions at a high level.

It aims also at providing cultures usable as models for study of the functions of the liver in biological and biochemical applications.

The human hepatocyte culture process of the invention is characterized in that there is associated, with a hepatocyte culture, cells of hepatic origin, different from the hepatocytes, of the type ensuring in vivo specific cell interactions with the hepatocytes.

In such a co-culture system, the cells of hepatic origin employed, multiply and come into confluence with the hepatocytes, thus ensuring the establishment of numerous contacts between the two types of cells.

Unexpectedly, taking into account the numerous parameters intervening in vivo in intercellular relationships, it is observed that there results from the in vitro interactions between these two types of cells, a prolonged survival of the hepatocytes and maintenance at a high level of their specific functions during this survival.

These results constitute a considerable advantage with respect to the state of the technique.

The interest of such a functional stability in the long-term, which permits, in particular evaluating the effects, over a long period, of medicaments, potential carcinogens and the study of various disorders, will in fact, be understood.

The cells of hepatic origin are advantageously selected from among cells cooperating in vivo with the hepatocytes.

Preferred cells of this type are constituted by cells of the same nature as hepatocytes, namely epithelial cells.

The cells of hepatic origin defined above are derived more particularly from lines obtained from animals, especially small rodent mammals, particularly, taking into account their easy availability, the rat.

Rat epithelial cells especially employed are formed from epithelial cells such as described by GUGUEN-GUILLOUZO et al in *Exp. Cell Research* 143 (1983) 47–54. These epithelial cells are probably of biliary origin.

The originality of such models of co-cultures of cells derived from different species will be appreciated.

It is known, in fact, that there are numerous problems of species specificities and even tissue specificities encountered in culture systems.

Now according to the invention, it is established that human hepatocytes, associated with the hepatic cells of animal origin and more especially, as shown in the examples with rat hepatic cells, survive at least six to eight weeks and maintain several differentiated functions such as albumin secretion and the conjugation of medicaments.

According to another feature of the invention, after the aggregation of the two types of cells, there is added into the culture medium employed a hormone more especially of the corticosteroid type such as hydrocortisone hemisuccinate. This hormone has advantageously the effect of participating in the cell interactions. As a result there is a stabilization of the hepatocytes in the culture, specifically of their specific functions.

According to yet another additional feature of the invention, the hepatocytes are separated from the co-cultures thus obtained.

For this purpose, the co-cultures are subjected to the action of a proteolytic enzyme of collagenase type, in the absence of its co-factor, calcium.

One proceeds advantageously under conditions enabling a slow action of the enzyme, in particular, at a temperature on the order of 37° C.

Although numerous studies have shown the difficulty of separating various cell types in heterogeneous cell culture, the invention provides means enabling separation selectively of the hepatocytes from the co-culture.

Thus there is provided a purified hepatocyte population, stabilized by the co-culture, of great interest for numerous applications in biochemistry and molecular biology, in particular, for the study of the expression of genes.

After washing, the hepatocytes which have been separated from the co-cultures may be either frozen or preserved at least about at $-80°$ C. for subsequent use, or reseeded with new hepatic cell cultures, which further increases their life span.

In a preferred embodiment of the invention, cells of hepatic origin are added to the hepatocytes after the attachment of the later to the supports used. For the seeding of the hepatocytes, operations are, advantageously, performed under the usual conditions, employing supports of an organic material such as polystyrene.

The human hepatocytes used are derived from adult livers or normal or pathological foeti, which permits several models to be available for studies in pharmacology or pathology. It is also interesting to note that with hepatocytes derived from fetal livers, after some weeks of co-culture there is obtained a maturation of the type which is produced in vivo. The invention thus represents a means of studying hepatic differentiation.

The cells of hepatic origin employed are advantageously constituted, as indicated above, of rat epithelial cells probably of biliary origin.

For studies concerning the metabolism of a normal liver, recourse has more particularly been made to untransformed cells.

However, it is known that these cells are transformed spontaneously after several months. They then modify the signal given to the hepatocyte to stabilize it. The use of such transformed cells is interesting as a model for studying very early alterations particularly in hepatocarcinogenesis.

The culture medium contains nutrient substances generally used for hepatocyte cultures.

It appears, in addition, appropriate to incorporate therein insulin which facilitates the expression of hepatocyte functions.

Advantageously albumin is also used which has the effect, particularly, of stabilizing the membranes as well as the spreading of the cells which are better adapted then to the culture conditions.

Another suitable additive in these culture media is constituted by calf serum.

This medium is advantageously renewed during the co-culture. In particular, it is appropriate to renew this medium, particularly daily or every other day. This medium can contain serum. However, advantageously, medium not containing serum is used, hence better defined as to its composition and the effects resulting therefrom.

Into this culture medium used, after the confluence of the hepatic cells, a corticosteroid is added, advantageously hydrocortisone hemisuccinate, in particular at doses of $7 \times 10^{-5}$M to $7 \times 10^{-7}$M corresponding to an interval determined by the toxicity which could appear with respect to the cultures and the physiological concentration.

When it is desired to isolate the hepatocytes from the co-culture, the latter is subjected to the action of collagenase in the absence of calcium.

The absence of this cation is known to result in the modification of the adhesivity and the form of numerous cell types.

The conditions employed in the invention are such that its absence is without effect only on the rat epithelial cells.

The collagenase having a reduced activity acts preferentially on the easily accessible collagen, that is to say on the collagen located between the two cell types, which results in the preferential detachment of the hepatocyte groups.

Advantageously this step is carried out by operating an incubation of the co-culture previously washed with a buffer in order to remove any trace of calcium. A concentration of about 0.020 to 0.030% of collagenase in buffered solution devoid of calcium is used and the reaction medium is maintained at about 37° C. for about 15 min. The hepatocytes are recovered by subjecting the medium to mechanical stirring and then centrifugation and the hepatocytes are advantageously washed to remove the enzyme.

In another preferred embodiment, the cells of hepatic origin defined above are added to pure hepatocyte populations after several days of culture.

This feature enables the function of the hepatocytes to be modulated, that is to say the genes to be reactivated.

It is thus possible to modify the activity observed with a conventional hepatocyte culture, where the hepatocyte is in culture alone, by the late addition of epithelial cells and to raise, for example, the albumin production which had practically entirely disappeared.

The co-culture is then advantageously pursued under the above conditions.

The invention is also directed at human hepatocyte cultures as novel products.

These co-cultures are characterised by the presence of numerous fibers of reticulin from about 24 hours after the confluence of the cells of hepatic origin.

They are also characterised by a functional stability of the hepatocytes, with respect to their specific functions, of at least 6 to 8 weeks.

In a preferred embodiment of the invention the co-cultures comprise human hepatocytes in association with hepatic cells that derive from small mammals.

This relates particularly to hepatic cells of small rodent mammals, in particular, from rats.

Such cultures are characterised by the presence of extracellular material around the hepatocytes and between the hepatocyte and the hepatic cells.

It is a heterogeneous material formed essentially from fibronectin and collagens.

In the co-cultures comprising hepatocytes derived from normal livers the collagen precipitates and forms reticulated fibers as in vivo (although it remains practically entirely soluble in the medium in the case of pure hepatocyte cultures of the prior art).

This collagen is then formed principally from collagen III and comprises in lesser amount collagen I which translates into good functioning of the cells.

In parallel, these co-cultures are characterised by the maintenance at a high level of their hepatocyte functions.

In particular, the hepatocyte cells of these co-cultures are capable of producing albumin for at least four weeks.

The establishment of this albumin production by immunoperoxidase has enabled the observation of a polarity of the albumin as in vivo, that is to say a concentration of the Golgian vesicules containing albumin towards one pole of the cell.

Study of the glucuronidation path shows in addition an activity of the latter for at least 3 weeks.

There is observed, on the contrary, in the extracellular material a predominance of collagen I and small amounts of collagen III when the albumin secretion is itself reduced beyond especially 6 to 8 weeks of culture.

This change can reflect the known in vivo behavior of pathological livers.

The long term maintenance of the specific hepatocyte functions in human hepatocytes cultivated in co-culture enables numerous biological and biochemical applications to be envisiged.

The models constituted by these co-cultures are usable, particularly in cancerology for mutagenesis and carcinogenesis tests; in pharmacology for tests of acute or chronic hepatotoxicity of medicaments, of hepatic biotransformation of a new molecule (in the course of the period of research and development of a pharmacologically active principle) also in biotechnology for the production of metabolites of medicaments, of human plasma proteins (in particular albumin and coagulation factors), of hepatic supply factors, usable in cases of great hepatic cell insufficiency production of viral antigens (in particular those of the hepatitus B virus).

Other features and advantages of the invention will appear in the examples which follow and by referring to FIGS. 1 to 6.

BRIEF DESCRIPTION OF DRAWINGS

The FIG. 1a shows a photo by optical microscope (enlargement 120) showing the extracellular material after dyeing of reticulin (a).

FIG. 5 shows the formula of ketotifene and of its metabolites, and.

EXAMPLE 1

Figure 1A:
FIGS. 1b and 1c, the photos obtained by immunofluorescence after 22 days of culture, showing respectively the fibronectin (1b) and the collagen III (1c).

Process of Co-Culture of Human Hepatocytes and Rat Hepatic Cells

Under a) are reported the means used for taking up the human hepatocytes and under b) the conditions employed for the co-culture.

a) Taking-Up of the Hepatocytes

The operation is at the end of binephrectomy for renal transplantation by the technique described by GUGUEN-GUILLOUZO et al in *Cell. Biol. Int. Rep.* 1982, 6, 625-628 "High yield preparation of isolated human adult hepatocytes by enzymatic perfusion of the liver."

The human hepatocytes are obtained from either hepatic tissue fragments (5-10 g) or from a portion of the whole liver (left lobe). The tissue is dissociated by perfusion from a collagenase solution via the portal vein. The freshly isolated hepatocytes show the ultrastructure characteristics of in vivo parenchyma cells. The process of isolation above does not result in any obvious nuclear or cytoplasmic alteration.

The cellular yield is of the order of $10^9$ hepatocytes and the viability of the cells of the order of 85%.

The isolated hepatocytes are washed and purified before being placed in culture.

b) Co-Culture

The hepatocytes are then seeded in polystyrene bottles with or without a coating of purified fibronectin from human plasma.

The seeding is carried out in the proportion of $0.5 \times 10^6$ cells per ml of culture medium.

HamF$_{12}$ medium is used containing 10 $\mu$g/ml of pig insulin, 0.2% of bovine albumin and 10% of fetal calf serum. About 3 hours later, the time necessary for the attachment of 60 to 70% of the hepatocyte substrate, the nutrient medium is removed and replaced by identical fresh nutrient medium containing $0.8 \times 10^6$ rat hepatic epithelial cells per ml. These cells are derived from lineages obtained by dissociation of the 10 day old rat liver by means of trypsin solution. They are used before their spontaneous transformation in vitro, easily recognizable by various criteria as reported by MOREL-CHANY E. et al in "Spontaneous neoplastic transformation in vitro of epithelial cell strains of rat liver: cytology, growth and enzymatic activities." Europ.3. Cancer, 1978, 14 1341-1352.

In the course of the subsequent hours, the hepatocytes are spread out to constitute spans of granular epithelial cells. The rat hepatic epithelial cells proliferate and rapidly occupy all the free spaces.

After 24-30 h a cellular confluence is reached. The nutrient medium is renewed every day or every 2 days. When the cellular confluence is reached, there is added to this medium $3.6 \times 10^{-5}$M or hydrocortisone hemisuccinate. From this moment the presence of serum is not necessary.

Under these conditions, the hepatocytes survive without obvious cell loss for at least 6 to 8 weeks with maintenance at a high level of various specific functions. No obvious proliferation of hepatocytes or of rat epithelial cells, nor detachment of a significant number of the hepatocytes is observed.

There is noted, by electronic microscope study, the production of considerable extra-cellular material.

This material comprises numerous fibres which appear from 24 h after the cellular confluence and are localized between the two cell populations and between the hepatocytes.

There is also noted the presence in a considerable amount of fibronectin and collagen type III. On the other hand, only small amounts of collagen type I around the hepatocytes are observed. There is also found collagen of type IV and laminin.

Figure 1B:
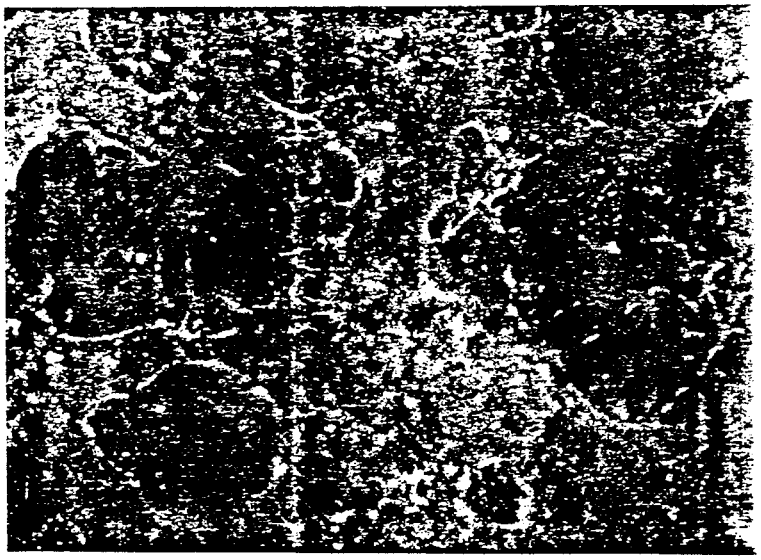
Figure 1C:

FIG. 1 corresponds to a photo taken by the optical microscope (enlargement 120) in which the extracellular material concerned appears after dyeing of reticulin after 6 days of culture (a) and where there is localized fibronectin (b) and collagen of type III (c) by indirect immunofluorescence after 22 days of culture.

COMPARATIVE EXAMPLE 1A

Culture of Human Hepatocytes by a Conventional Technique

Polystyrene bottles with or without a purified fibronectin coating from human plasma are covered by means of hepatocytes taken up as indicated in Example 1.

The seeding is carried out in the proportion of $2 \times 10^6$ cells per bottle in 3 ml of culture medium used also for the above seeding but into which is added $5 \times 10^{-5}$M of hydrocortisone hemisuccinate. This medium is renewed 4 h after the seeding, then each day.

Electron microscope studied only shows few reticular fibres between the cells.

EXAMPLE 2

Comparison Between the Morphological Characteristics and the Functional Activities of the Hepatocytes in Co-Culture (According to Example 1) or in Conventional Culture (According to Comparative Example 1A

Morphological Characteristics

By using the usual culture conditions, a rapid spreading of hepatocytes is observed particularly when bottles coated with fibronectin are used.

Figure 2A:
FIGS. 2a and 2b show photos taken with the phase contrast microscope, respectively of hepatocyte cultures alone and of co-cultures according to the invention.

As is shown in FIG. 2a, mono-layers of granular epithelial cells are formed with refringent intercellular spaces corresponding to structures of the biliary canalicule type. This figure corresponds to a photo taken after 4 days of culture, at an enlargement of 290 with a phase contrast microscope. The survival of these cells does not exceed 2 to 3 weeks. The examination of these cells at the ultrastructural level shows, after some days, a gradual reduction in the glycogen particles and in the granular endoplasmic reticulum accompanied by a rapid increase in the elements of the cytoskeleton in particular under the plasma membrane.

Figure 2B:

On the other hand, as shown by examination of FIG. 2b, the hepatocytes obtained by the process of co-culture of the invention are less spread out than in the case of conventional culture. FIG. 2b corresponds to a photo of the cultures aged 10 days taken with the phase contrast microscope (enlargement 200).

The examination of this photo enables structures of the biliary canalicule type to be observed. It is noted that the particles of glycogen remain abundant and the GOLGI complexes are localized close to structures of the biliary canal type.

Figure 3:
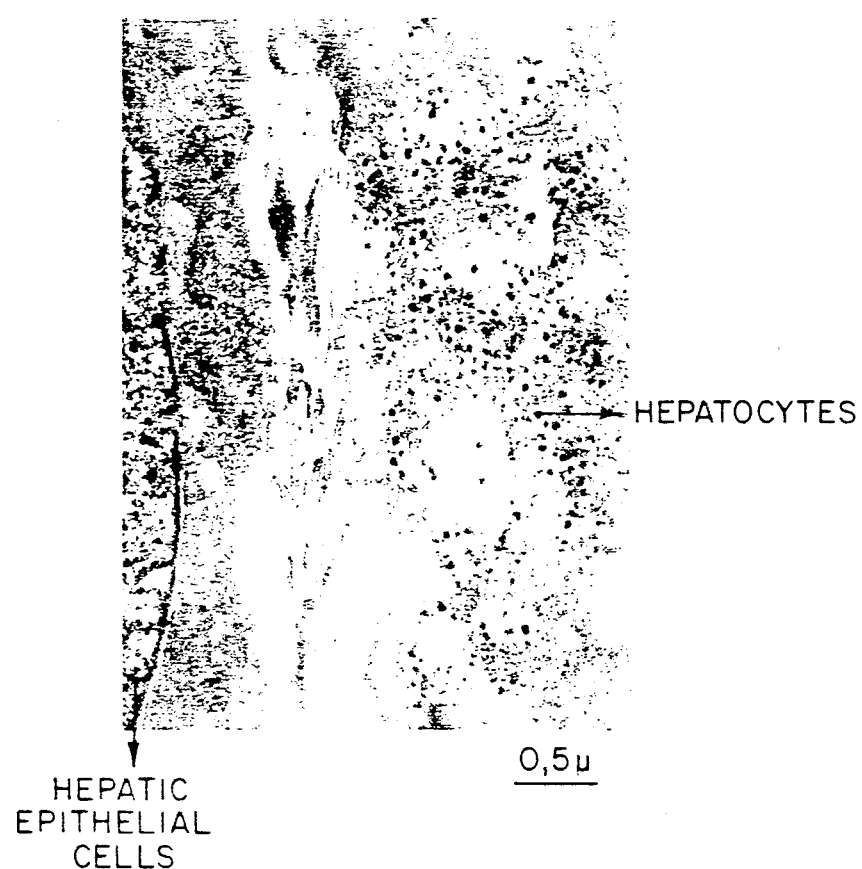
FIG. 3 shows a photo taken with the electron microscope of co-cultures of the invention showing collagen fibers between two cellular types.

The photo exhibited in FIG. 3, taken with the electron microscope after 30 days of culture (enlargement 31,000), enables numerous contacts to be observed between the two cell populations and filamentous structures comprising typical collagen fibres appearing in the intracellular spaces (see arrow).

Functional Activities

Albumin Secretion

Albumin secretion was studied as a function of time, with hepatocytes of conventional cultures (H) and hepatocytes of co-culture (HC) in a serum-free medium.

Figure 4:
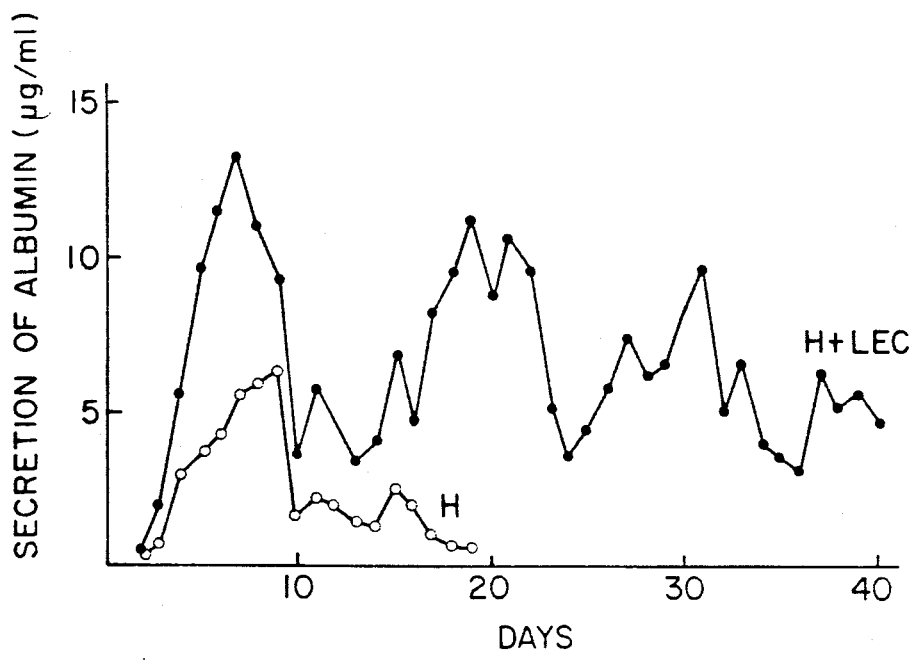
FIG. 4 shows a curve of the variation of the albumin concentration as a function of time with conventional cultures on the one hand and the co-cultures of the invention on the other hand.

In FIG. 4, are reported the results respectively obtained corresponding to the average of two experiments. The curves •——• and ○——○ correspond respectively to the use of HC and H in the absence of calf serum.

With customary culture conditions an increase in the albumin secretion is observed as a function of time during the first 8 days, followed by a diminution.

In the case of the co-cultures, the speed of albumin secretion proved higher and remained at a high level for several weeks, even in the absence of serum. By using the technique of immunoperoxidase, albumin production was demonstrated for the majority of the hepatocytes during at least the 4 first weeks of culture.

Modulation of Albumin Production

Single cultures of human hepatocytes in the presence or in the absence of fetal calf serum were used.

After 4 days of culture, the albumin production was low, practically nil.

By adding rat hepatic epithelial cells according to the invention, a resumption in albumin production was noted which then reached a high level.

The use of the co-cultures of the invention hence enables reactivation of the specific functions of the hepatocytes.

Biotransformation of Ketotifene

Ketotifene marketed under the mark ZADITEN by SANDOZ laboratories is a medicament administered orally with anaphylactic action.

This medicament was selected for this study by reason of its metabolism along different typical routes as described by GUERRET et al in Proceedings 1 st Eur. Cong. Biopharm. Clermont-Ferrand, vol. I, p. 317, Techn. et Doc. (1981).

The study of this biotransformation (which will be reported in more detail in Example 3 below) shows that the glucuronidation path remains the most active for at least 3 weeks with hepatocytes in co-cultures whereas it disappears after 4 days with the conventional hepatocyte cultures.

EXAMPLE 3

Application of Adult Human Hepatocyte Cultures as a Model for the Study of the Metabolism of Medicaments In man, ketotifene is transformed by several metabolic paths, undergoing N-demethylation, N-oxidation, N-glucuroconjugation leading to a quaternary ammonium derivative and to a reduction of the keto groups followed by O-glucuronidation. This biotransformation is described in the article of GUERET et al mentioned above.

In FIG. 6, are reported the formulae of ketotifene and of the metabolites obtained. These formulae bear numbers 1 to 6 and correspond respectively: 1) to ketotifene, 2) to reduced ketotifene, 3) to N-glucuroketotifene, 4) to non-ketotifene, 5) to reduced non-ketotifene and 6) to oxidized ketotifene.

At different intervals of time after the seeding of the cells, between 24 h and 3 weeks, the adult hepatocytes from a culture carried out according to Example 1 with 3 $\mu$g/ml of ketotifene—$^{14}$C having a specific activity of 107 $\mu$Ci/mg and 20 $\mu$g/ml of unmarked medicament per 25 cm of bottle, are incubated.

No toxicity at this concentration of medicament (23 $\mu$g/ml of medium) is observed.

Four hours or 24 hours after the addition of medicament, aliquots of medium are collected which are rapidly frozen and stored at $-20°$ C. until analysis. The metabolites of the ketotifene are analyzed by reverse-phase high performance liquid phase chromatography (HPLC). Their structure is confirmed by mass spectrometry.

hepatocytes of co-cultures, the metabolism of the ketotifene is effected more actively.

| CELLS | CULTURE PERIOD (days) | KETOTIFENE unmodified | | METABOLIZED KETOTIFENE | | | | RATIO $\frac{G}{R-G}$ |
|---|---|---|---|---|---|---|---|---|
| | | | | REDUCED (F) | | N-GLUCURONIDE (G) | | |
| | | a | b | a | b | a | b | b |
| HEPATOCYTES | 0.17 | 67 | 25 | 33 | 45 | 0 | 25 | 0.34 |
| " | 1 | 68 | 16 | 32 | 56 | 0 | 28 | 0.33 |
| " | 4 | 63 | 13 | 37 | 61 | 0 | 26 | 0.30 |
| " | 6 | 93 | 50 | 7 | 50 | 0 | 0 | 0.00 |
| HEPATOCYTES – LIVER epithelial cells | 4 | 58 | 13 | 42 | 43 | 0 | 44 | 0.51 |
| HEPATOCYTES – LIVER epithelial cells | 7 | 51 | 6 | 49 | 29 | 0 | 65 | 0.69 |
| HEPATOCYTES – LIVER epithelial cells | 21 | 83 | 29 | 17 | 59 | 0 | 12 | 0.17 |
| Liver epithelial cells | | 100 | 100 | 0 | 0 | 0 | 0 | |

The detection limit of radioactivity is 400 dpm which corresponds to 0.13 ng of $^{14}C$-ketotifene.

The time of retention of the metabolites which are similar in the two experiments are compared with those obtained with synthetic compounds.

The metabolites are collected for the purposes of study by mass spectrometry.

In the same way, similar medicaments and their metabolites before and after incubation of $\beta$-glucuronidase, are analyzed.

The experiments carried out have shown that whatever the culture type, no glucuronides of ketotifene are detected before 8 hours following the addition of medicament.

Figure 5:
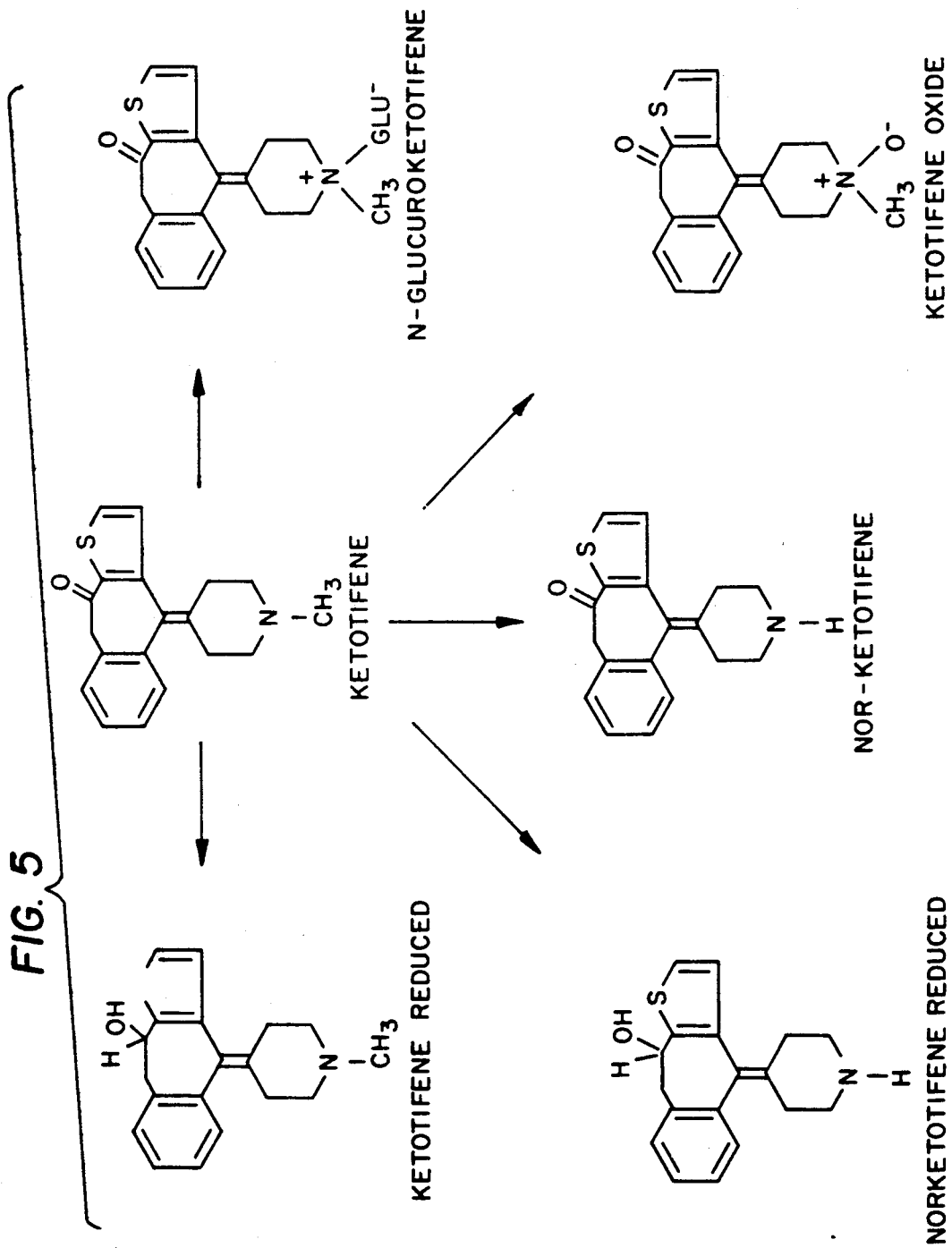

Between 4 and 28 h after the seeding of the cells incubated with the ketotifene, there are obtained, as shown in FIG. 5, the following metabolites in the culture medium, namely non ketotifene: this product possesses the longest retention time in HPLC (74) and gives a characteristic molecular ion at m/e 295 in GLC-MS;

traces of ketotifene N-oxide which is decomposed on GLC-MS analysis giving an unmodified medicament.

reduced ketotifene constituting the principal metabolite: this product possesses in HPLC a retention time identical with that of the synthetic reference compound obtained by reduction of ketotifene with sodium borohydride. On GLC-MC analysis, the molecular ions and other ionic characteristics are observed at m/e 311 and m/e 291 respectively $[M^+ -18(H_2O)]$.

reduced non-ketotifene giving in GLC-MS a characteristic fragment ion at m/e 279 $[M^+ -18(H_2O)]$ glucuronides both from the unmodified medicament (N-glucuro-ketotifene) and the reduced ketotifene, also obtained in considerable amounts between 20 and 25 min in HPLC.

These products lead to ketotifene and to its free reduced derivative after incubation with $\beta$-glucuronidase. Also found are small amounts of glucuronide of reduced non-ketotifene.

These various metabolites correspond to the 4 metabolic routes found in vivo, namely N-demethylation, N-oxidation and principally ketoreduction and N-glucuronidation.

The two latter routes are used in order to determine the metabolic activity of the cell cultivated alone or in association with liver epithelial cells for 24 h or more.

After incubation of 4 h of ketotifene and human culture hepatocytes, the speed of metabolism appears slightly modified the first 7 days in both cases. With The speed of the metabolism is considerably reduced with older cultures. It appears however much higher on the 25th day of co-culture than on the 6th day of conventional culture.

The table below includes the results relating to the respective percentages of an unmodified ketotifene, reduced ketotifene and ketotifene N-glucuronide obtained 4 h and 24 h after the addition of medicament.

The values indicated correspond to the average of two tests.

As shown by the examination of this table, with conventional cultures, the ratio of the number of the glucuronide metabolites to the number of the total metabolites (reduced metabolites and N-glucuronide) is from 0.34 to 0.30 the first 4 days.

The 6th day glucuronidation activity is no longer noted whereas one still observes a reduction.

With the co-cultures, the ketotifene is actively metabolized for the period studied of 21 days.

At the 7th day, the ratio glucuronide metabolite: total metabolites is 0.69 and at the 21st day this ratio is still 0.17.

At this moment, the percentage reduction of total ketotifene is identical with that found in conventional cultures after 24 h.

During the 24 days of co-culture non-ketotifene is detected.

In the epithelial cell cultures used as control, no biotransformation into ketotifene is detected.

EXAMPLE 4

Production of Viral Antigens

Normal human hepatocyte cultures were infected experimentally with hepatitis B virus.

Once infected, production of the viral $Hb_s$ and $Hb_e$ antigens characteristic of the virus was demonstrated.

The study carried out has also shown the maintenance in the long term at a higher level than in the infected cultures of the prior art, of the production of these antigens for at least 3 weeks.

The maintained production of $Hb_e$ shows a replication of the virus.

The human hepatocyte co-cultures of the invention hence provide valuable models particularly for the study of the factors involved in the recognition of the virus of the target cell.

According to another aspect, they also constitute means of great interest for the production of viral antigens and specific antibodies in large amount.

EXAMPLE 5

Separation of the Hepatocytes from a Co-culture of Human Hepatocytes and Rat Epithelial Cells A co-culture of the type of Example 1 was subjected to two successive washings in order to remove any trace of calcium from the culture medium. A saline solution of the PBS (phosphate borate sodium buffer) type, devoid of calcium and magnesium was used.

An incubation was performed at 37° C. for 15 min. on the co-culture with an aqueous collagenase solution prepared in a concentration of 0.025% in a buffer solution itself devoid of calcium.

The co-culture was subjected to mechanical stirring to detach the hepatocytes. The latter were collected by centrifugation, and then they were placed in suspension and washed to remove the collagenase.

The isolated hepatocytes were immediately used for further cultures or frozen for preservation.

Figure 6A:
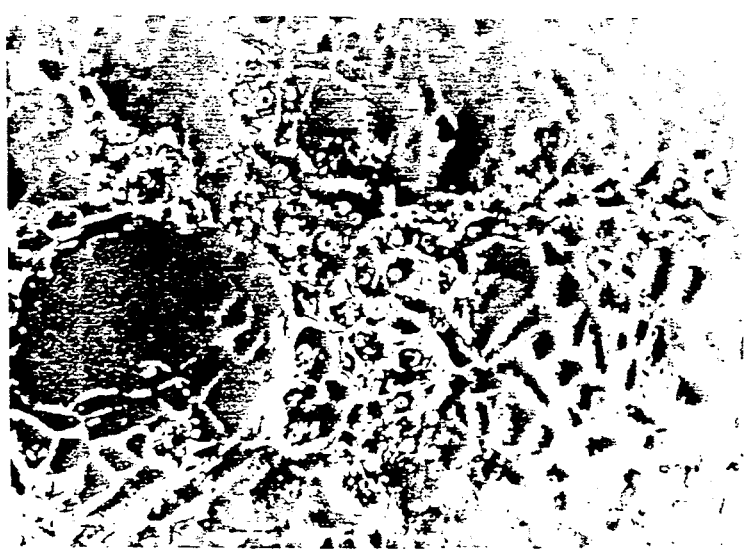
FIGS. 6a to 6c exhibit photos with the microscope showing respectively hepatocyte cells being detached from the co-culture, isolated hepatocytes and areas left free in the co-culture after separation of the hepatocytes.
Figure 6B:
Figure 6C:
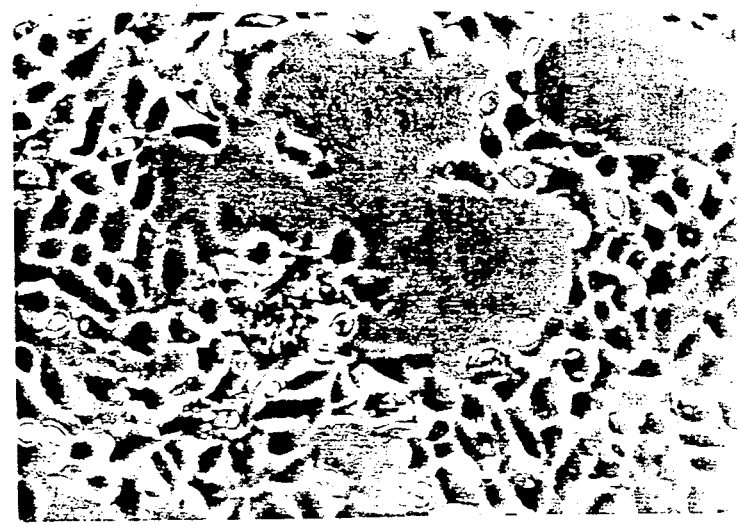

In FIGS. 6a to 6c, are shown respectively the hepatocyte populations being detached under the action of the collagenase of the co-culture (6a) the separated populations (6b) and the remaining culture with the areas left free by the removal of the hepatocytes (6c).

We claim:

1. A method of culturing human hepatocytes comprising combining a first cell population comprising a culture of human hepatocytes including a medium, and a second cell population of mammalian epithelial cells of hepatic origin, said second cell population being from a different species with respect to said first cell population, cells of said second cell population being capable of forming numerous contacts with cells of said first cell population, whereby a co-culture is formed in which filamentous structures comprising collagen fibers appear in the intracellular spaces.

2. A method according to claim 1, wherein said epithelial hepatic cells are derived from established cell lines obtained from mammals.

3. A method according to claim 1 wherein said cells of hepatic origin are transformed cells.

4. A method according to claim 1 wherein said cells of hepatic origin are untransformed cells.

5. A method according to claim 1 wherein said human hepatocytes are obtained from livers of a human adult.

6. A method according to claim 1 wherein said human hepatocytes are obtained from livers of a human fetus.

7. A method according to claim 1 wherein said human hepatocytes are obtained from normal livers.

8. A method according to claim 1 wherein said human hepatocytes are obtained from pathological livers.

9. A method according to claim 1, further comprising after the combination step, the step of adding into the co-culture a hormone of the corticosteroid type.

10. A method according to claim 9 wherein said hormone is hydrocortisone hemisuccinate.

11. A method according to claim 9 wherein the adding step comprises the step of adding the hormone after aggregation of said hepatocytes and said cells of hepatic origin.

12. A method according to claim 10, wherein said adding step comprises adding a culture medium containing approximately $7 \times 10^{-5}$M to $7 \times 10^{-7}$M of hydrocortisone hemisuccinate.

13. A method according to claim 1 wherein said medium is serum-free.

14. A method according to claim 1 wherein said medium contains pig insulin, bovine albumin, and serum.

15. A method according to claim 14 wherein said serum is fetal calf serum.

16. A method according to claim 1, further comprising the step of selectively detaching said hepatocytes from said co-culture by incubation of said co-culture with a proteolytic enzyme capable of hydrolyzing collagen fibers in a medium without calcium, under conditions permitting slow action of said enzyme specific with respect to the hepatocyte populations, and then, subjecting the medium to stirring and centrifugation to remove the detached hepatocytes from the medium.

17. A method according to claim 16 wherein said proteolytic enzyme is collagenase.

18. A method according to claim 17 wherein the incubation of said co-culture is performed with collagenase at about 37° C. for about 15 min., at a concentration of about 0.020 to 0.30% in buffered solution without calcium.

19. A method according to claim 1 wherein the combining step comprises adding said cells of hepatic origin to the hepatocyte culture upon aggregation of said hepatocyte culture.

20. A method according to claim 1 wherein said combining step comprises adding said cells of hepatic origin to said hepatocytes after said hepatocytes have been placed in culture.

21. A method according to claim 1, wherein said combining step comprises adding said cells of hepatic origin to pure hepatocyte populations after several days of culture, thus permitting the functions of said hepatocytes to be modulated.

22. An in vitro human hepatocyte co-culture capable of maintaining functioning hepatocytes for six weeks, comprising human hepatocytes and mammalian epithelial cells of hepatic origin but different from said hepatocytes and from a different species, said epithelial cells forming numerous contacts with the human hepatocyte cells.

23. A co-culture according to claim 22, further comprising numerous reticulin fibres formed about 24 hours after confluence of said cells of hepatic origin.

24. A co-culture according to claim 22 wherein said co-culture includes a heterogeneous extracellular material, formed essentially from fibronectin and collagen, around said hepatocytes and between said hepatocytes and said hepatic cells.

25. A method of culturing human hepatocytes comprising combining a first cell population comprising a culture of human hepatocytes including a medium, and a second cell population of hepatic origin, said second cell population being epithelial hepatic cells derived from cell lines obtained from rats, cells of said second cell population being capable of forming numerous contacts with cells of said first cell population, whereby a co-culture is formed in which filamentous structures comprising collagen fibers appear in the intracellular spaces.

26. An in vitro human hepatocyte co-culture capable of maintaining functioning hepatocytes for six weeks, comprising human hepatocytes and cells of hepatic origin which are rat epithelial cells said cells forming numerous contacts with said hepatocytes, and a heterogeneous extracellular material, formed essentially from fibronectin and collagen, around said hepatocytes and between said hepatocytes and said hepatic cells.

27. A co-culture according to claim 6, wherein said co-culture comprises hepatocytes from normal livers and wherein said collagen is formed of collagen III and collagen I.

* * * * *

UNITED STATES PATENT AND TRADEMARK OFFICE
CERTIFICATE OF CORRECTION

PATENT NO. : 5,112,757
DATED : May 12, 1992
INVENTOR(S) : GUGUEN-GUILLOUZO, Christiane; GUILLOUZO, Andre; BOUREL, Michel It is certified that error appears in the above-indentified patent and that said Letters Patent is hereby corrected as shown below:

Title page, column 1 under heading "[30] Foreign Application Priority Date", kindly add
 --April 29, 1984 [PCT]..........PCT/FR84/00118--;
Title page, column 2, under "U.S. Patent Documents", kindly add
 --4,352,887 10/1982 Reid et al......435/240--;
Title page, column 2, under "References Cited", add the following heading and citation:
 --FOREIGN PATENT DOCUMENTS June 4, 1971 [FR] France....2059471--;
Title page, column 2, under "Other Publications", kindly add
 --Sakahibara et al Chem. Abs 88: 866672 (1978)--;

UNITED STATES PATENT AND TRADEMARK OFFICE
CERTIFICATE OF CORRECTION

PATENT NO. : 5,112,757

DATED : May 12, 1992

INVENTOR(S) : GUGUEN-GUILLOUZO, Christiane; GUILLOUZO, Andre; BOUREL, Michel

It is certified that error appears in the above-indentified patent and that said Letters Patent is hereby corrected as shown below:

Column 1, line 15, change "metabolism" to —the characterization of the metabolic paths—;

Column 8, line 54, two occurrences, change "non-ketotifene" to
    —nor-ketotifene—; and Column 9, line 37, Column 9, line 49, and Column 10, line 48, change "non-ketotifene" to
    —nor-ketotifene—.

Signed and Sealed this

Seventh Day of February, 1995

BRUCE LEHMAN

Attest:

*Attesting Officer*      *Commissioner of Patents and Trademarks*

UNITED STATES PATENT AND TRADEMARK OFFICE
CERTIFICATE OF CORRECTION

PATENT NO. : 5,112,757

DATED : May 12, 1992

INVENTOR(S) : Guguen-Guillouzo, et al.

It is certified that error appears in the above-indentified patent and that said Letters Patent is hereby corrected as shown below:

On the title page, item [73] Assignee, should read--

Institut National de la Sante et de la Recherche Medicale--.

Signed and Sealed this

Eighteenth Day of April, 1995

Attest:

BRUCE LEHMAN

*Attesting Officer*   *Commissioner of Patents and Trademarks*